United States Patent [19]

Behan et al.

[11] Patent Number: 5,891,729
[45] Date of Patent: Apr. 6, 1999

US005891729A

[54] METHOD FOR SUBSTRATE CLASSIFICATION

[75] Inventors: John Martin Behan, Kennington; Keith Douglas Perring, Ashford; Brian James Willis, Canterbury; Ian Michael Payne, Willesborough Ashford; Jennifer Valerie Oliver, Egerton Ashford, all of Great Britain

[73] Assignee: Quest International B.V., Naarden, Netherlands

[21] Appl. No.: 737,824

[22] PCT Filed: May 18, 1995

[86] PCT No.: PCT/GB95/01118

§ 371 Date: Aug. 5, 1997

§ 102(e) Date: Aug. 5, 1997

[87] PCT Pub. No.: WO95/32420

PCT Pub. Date: Nov. 30, 1995

[30] Foreign Application Priority Data

May 20, 1994 [EP] European Pat. Off. ............ 94303641

[51] Int. Cl.$^6$ .................. G01N 7/00; G01N 33/26
[52] U.S. Cl. ................... 436/2; 436/174; 73/23.41
[58] Field of Search .................. 436/2, 155, 159, 436/161, 174, 175, 901–903; 422/83, 89, 94; 73/23.41

[56] References Cited

U.S. PATENT DOCUMENTS 5,155,045  10/1992  Cutler et al. .................. 436/65
5,493,890  2/1996   Dussault et al. .............. 73/1 G

FOREIGN PATENT DOCUMENTS 03355  2/1993  WIPO .

*Primary Examiner*—Lyle A. Alexander
*Attorney, Agent, or Firm*—Pillsbury Madison & Sutro

[57] ABSTRACT

A substrate (e.g. skin of unknown type, fabric, or hard surfaces) is characterized by analyzing chemicals emanating from the substrate or from a substance (e.g. a test formulation comprising a mixture of volatile chemicals) applied to the substrate. Analysis is preferably done using a volatile chemicals sensor, desirably a sensor comprising an array of conducting polymer sensors. The chemical analysis data obtained in this way may be statistically analyzed, e.g. by Euclidian distance mapping or principal component analysis, for ease of handling. Having characterized a surface in this way, products, e.g. cosmetic and cleaning products, may be formulated for optimized performance on that substrate.

12 Claims, 12 Drawing Sheets

FIG. 2
REPORT
LAST FILE: C:\QUEST\FF.DBA
1) REF
FAB000.RAW 53.78 to 109.27 (s)
DATA PLOTTED
| SENSOR | INTENSITY | PATTERN | SD |
|---|---|---|---|
| 1 | 0.240 | 11.358 | 0.323 |
| 2 | 0.120 | 6.639 | 0.131 |
| 3 | 0.120 | 6.423 | 0.167 |
| 4 | 0.170 | 8.704 | 0.048 |
| 5 | 0.160 | 8.401 | 0.116 |
| 6 | 0.100 | 5.057 | 0.117 |
| 7 | -0.020 | -1.255 | 0.168 |
| 8 | -0.140 | -6.948 | 0.151 |
| 9 | 0.090 | 4.750 | 0.056 |
| 10 | 0.040 | 2.281 | 0.100 |
| 11 | 0.140 | 7.472 | 0.243 |
| 12 | -0.050 | -2.072 | 0.137 |
| 13 | -0.020 | -0.938 | 0.070 |
| 14 | 0.060 | 2.878 | 0.069 |
| 15 | 0.070 | 3.658 | 0.168 |
| 16 | 0.010 | 0.489 | 0.118 |
| 17 | 0.000 | 0.000 | 0.000 |
| 18 | 0.160 | 8.144 | 0.055 |
| 19 | 0.060 | 3.067 | 0.188 |
| 20 | 0.170 | 9.147 | 0.195 |
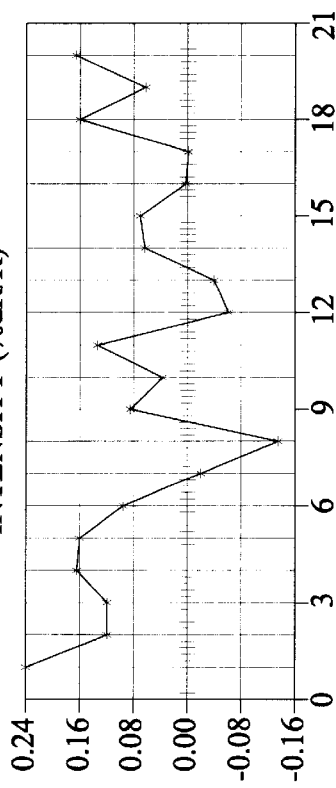
FIG. 2A
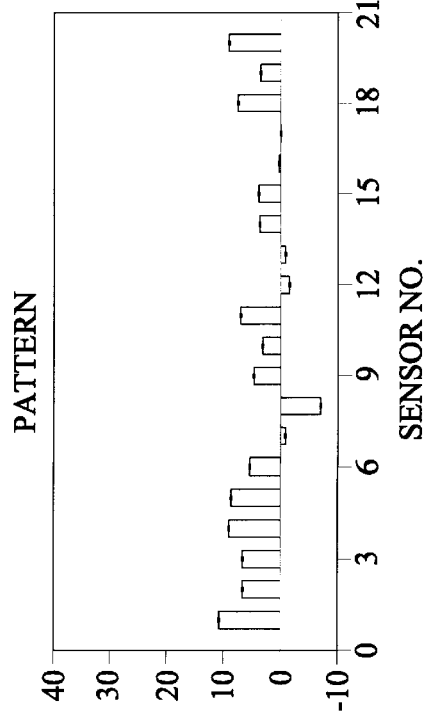
FIG. 2B

FIG. 3
REPORT
LAST FILE:
C:\QUEST\FF.DBA
2) AA
FAB001.RAW 43.72 to 88.84 (s)
DATA PLOTTED
| SENSOR | INTENSITY | PATTERN | SD |
|---|---|---|---|
| 1 | 0.170 | 8.628 | 0.529 |
| 2 | 0.140 | 7.578 | 0.336 |
| 3 | 0.120 | 6.735 | 0.264 |
| 4 | 0.110 | 6.136 | 0.286 |
| 5 | 0.080 | 5.418 | 0.421 |
| 6 | 0.080 | 4.896 | 0.146 |
| 7 | 0.050 | 3.383 | 0.255 |
| 8 | 0.030 | 2.516 | 0.329 |
| 9 | 0.050 | 3.628 | 0.226 |
| 10 | 0.030 | 2.804 | 0.330 |
| 11 | 0.130 | 7.132 | 0.264 |
| 12 | 0.040 | 2.614 | 0.150 |
| 13 | 0.040 | 3.213 | 0.291 |
| 14 | 0.040 | 3.076 | 0.280 |
| 15 | 0.060 | 3.688 | 0.156 |
| 16 | 0.090 | 4.824 | 0.287 |
| 17 | 0.090 | 4.778 | 0.283 |
| 18 | 0.120 | 6.424 | 0.406 |
| 19 | 0.090 | 4.816 | 0.180 |
| 20 | 0.150 | 7.601 | 0.623 |
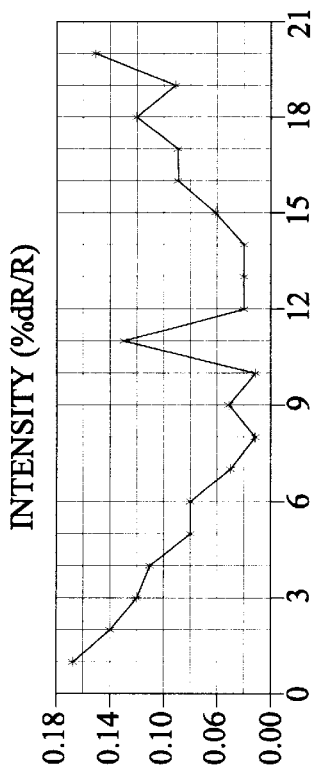
FIG. 3A
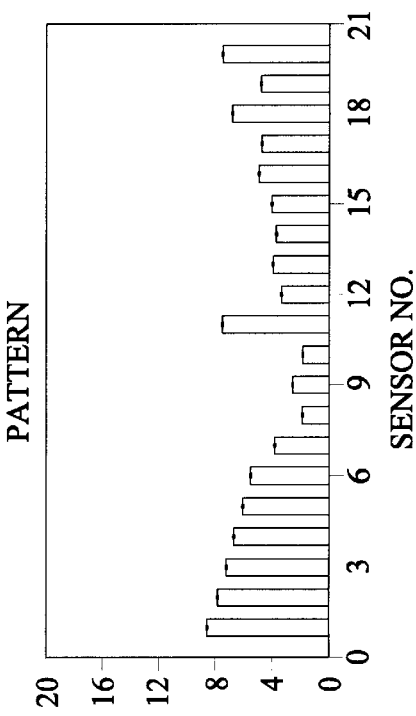
FIG. 3B

FIG. 4
REPORT
LAST FILE:
C:\QUEST\FF.DBA
4) CC
FAB003.RAW 30.25 to 81.15(s)
DATA PLOTTED
| SENSOR | INTENSITY | PATTERN | SD |
|---|---|---|---|
| 1 | -0.250 | -5.474 | 0.048 |
| 2 | -0.310 | -6.512 | 0.064 |
| 3 | -0.300 | -6.152 | 0.079 |
| 4 | -0.320 | -6.475 | 0.141 |
| 5 | -0.330 | -6.628 | 0.192 |
| 6 | -0.210 | -4.530 | 0.046 |
| 7 | -0.190 | -4.100 | 0.051 |
| 8 | -0.230 | -4.885 | 0.060 |
| 9 | -0.180 | -3.869 | 0.031 |
| 10 | -0.180 | -3.914 | 0.047 |
| 11 | -0.280 | -6.548 | 0.046 |
| 12 | -0.170 | -3.811 | 0.021 |
| 13 | -0.210 | -4.538 | 0.049 |
| 14 | -0.180 | -4.488 | 0.048 |
| 15 | -0.160 | -3.736 | 0.063 |
| 16 | -0.230 | -5.132 | 0.088 |
| 17 | -0.140 | -3.240 | 0.043 |
| 18 | -0.220 | -5.443 | 0.111 |
| 19 | -0.220 | -5.016 | 0.065 |
| 20 | -0.210 | -5.296 | 0.137 |
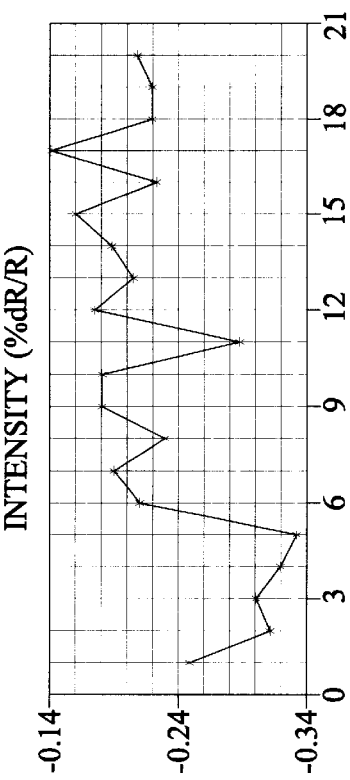
FIG. 4A
INTENSITY (%dR/R)
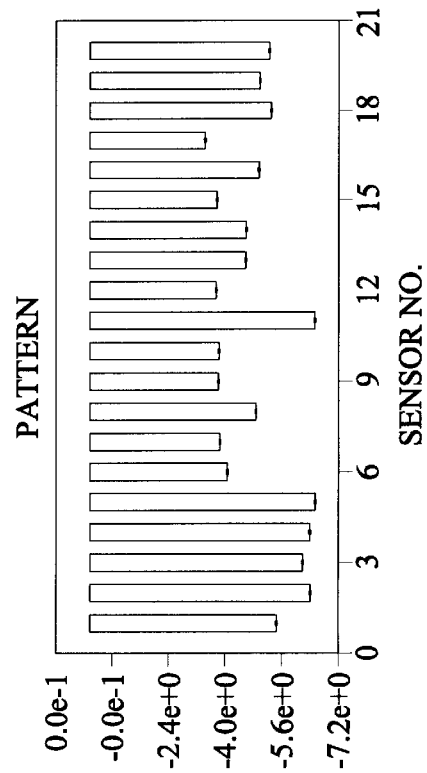
FIG. 4B
PATTERN
SENSOR NO.

FIG. 5
REPORT
LAST FILE:
C:\QUESTVFF.DBA
5) DD
FAB004.RAW 29.82 to 81.70(s)
DATA PLOTTED
| SENSOR | INTENSITY | PATTERN | SD |
|---|---|---|---|
| 1 | -0.230 | -6.880 | 0.104 |
| 2 | -0.240 | -6.281 | 0.057 |
| 3 | -0.250 | -6.687 | 0.026 |
| 4 | -0.230 | -6.858 | 0.147 |
| 5 | -0.270 | -7.033 | 0.187 |
| 6 | -0.180 | -5.007 | 0.038 |
| 7 | -0.180 | -5.313 | 0.132 |
| 8 | -0.130 | -3.685 | 0.055 |
| 9 | -0.150 | -4.234 | 0.053 |
| 10 | -0.130 | -3.488 | 0.045 |
| 11 | -0.250 | -6.708 | 0.018 |
| 12 | -0.130 | -3.510 | 0.021 |
| 13 | -0.170 | -4.820 | 0.070 |
| 14 | -0.170 | -4.674 | 0.068 |
| 15 | -0.170 | -4.808 | 0.090 |
| 16 | -0.150 | -4.027 | 0.087 |
| 17 | -0.150 | -4.183 | 0.104 |
| 18 | -0.200 | -5.182 | 0.070 |
| 19 | -0.110 | -3.010 | 0.069 |
| 20 | -0.210 | -5.590 | 0.038 |
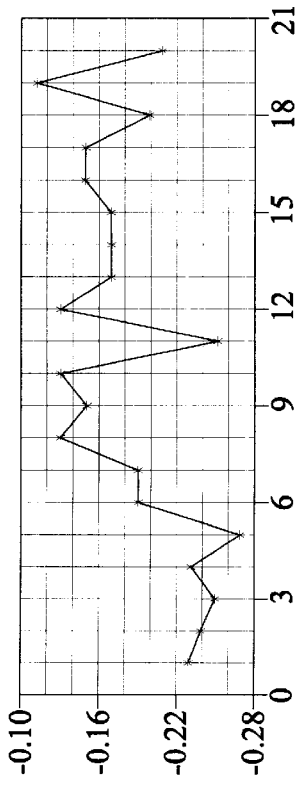
FIG. 5A
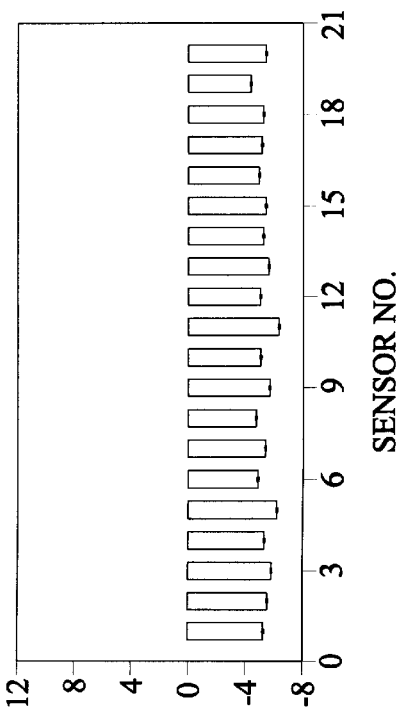
FIG. 5B

FIG. 6
REPORT
LAST FILE:
C:\QUEST\FF.DBA
8) EE
FAB005.RAW 27.23 to 53.15(s)
DATA PLOTTED
| SENSOR | INTENSITY | PATTERN | SD |
|---|---|---|---|
| 1 | -0.110 | -6.845 | 0.187 |
| 2 | -0.090 | -4.700 | 0.431 |
| 3 | -0.100 | -5.091 | 0.325 |
| 4 | -0.120 | -6.571 | 0.285 |
| 5 | -0.150 | -8.743 | 0.184 |
| 6 | -0.080 | -4.715 | 0.174 |
| 7 | -0.030 | -2.102 | 0.194 |
| 8 | -0.060 | -5.136 | 0.519 |
| 9 | -0.050 | -3.368 | 0.110 |
| 10 | -0.070 | -5.033 | 0.312 |
| 11 | -0.100 | -3.248 | 0.741 |
| 12 | -0.080 | -5.870 | 0.452 |
| 13 | -0.060 | -4.517 | 0.250 |
| 14 | -0.070 | -3.954 | 0.110 |
| 15 | -0.060 | -2.660 | 0.243 |
| 16 | -0.080 | -6.423 | 0.664 |
| 17 | -0.080 | -7.344 | 0.895 |
| 18 | -0.120 | -6.203 | 0.317 |
| 19 | -0.050 | -2.789 | 0.233 |
| 20 | -0.110 | -4.588 | 0.577 |
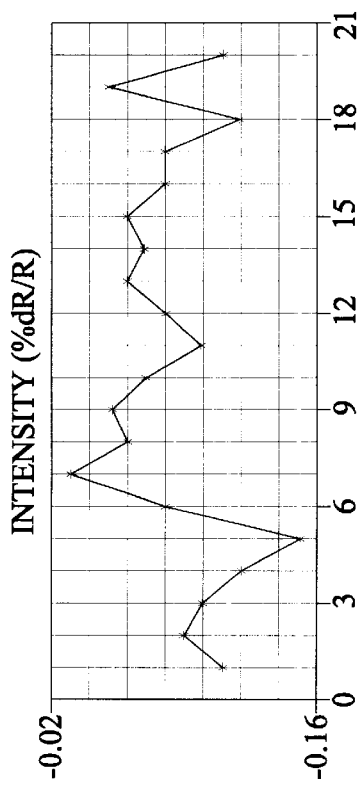
FIG. 6A
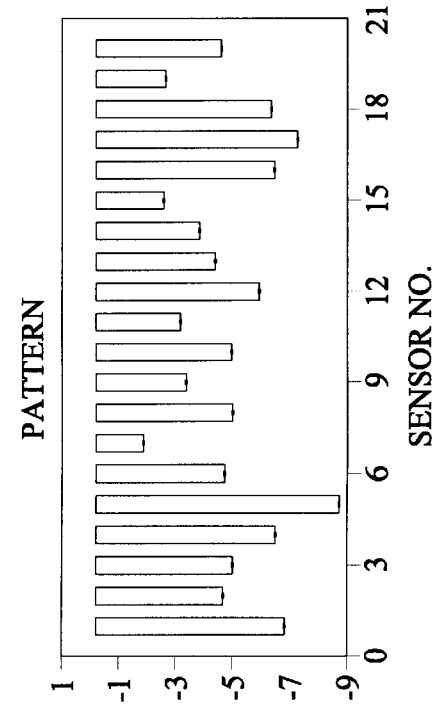
FIG. 6B

FIG. 7
REPORT
LAST FILE:
C:\QUEST\FF.DBA
7) FF
FAB006.RAW 28.98 to 58.28(s)
DATA PLOTTED
| SENSOR | INTENSITY | PATTERN | SD |
|---|---|---|---|
| 1 | -0.130 | -6.515 | 0.187 |
| 2 | -0.100 | -4.577 | 0.302 |
| 3 | -0.090 | -4.532 | 0.268 |
| 4 | -0.120 | -6.848 | 0.192 |
| 5 | -0.120 | -6.809 | 0.357 |
| 6 | -0.110 | -6.420 | 0.182 |
| 7 | -0.050 | -3.232 | 0.144 |
| 8 | -0.080 | -5.539 | 0.324 |
| 9 | -0.070 | -4.396 | 0.173 |
| 10 | -0.090 | -5.541 | 0.278 |
| 11 | -0.110 | -4.944 | 0.242 |
| 12 | -0.070 | -3.970 | 0.066 |
| 13 | -0.080 | -5.333 | 0.229 |
| 14 | -0.090 | -4.719 | 0.099 |
| 15 | -0.070 | -3.569 | 0.103 |
| 16 | -0.090 | -6.011 | 0.434 |
| 17 | -0.100 | -6.758 | 0.435 |
| 18 | -0.100 | -3.434 | 0.478 |
| 19 | -0.060 | -3.465 | 0.160 |
| 20 | -0.100 | -3.388 | 0.470 |
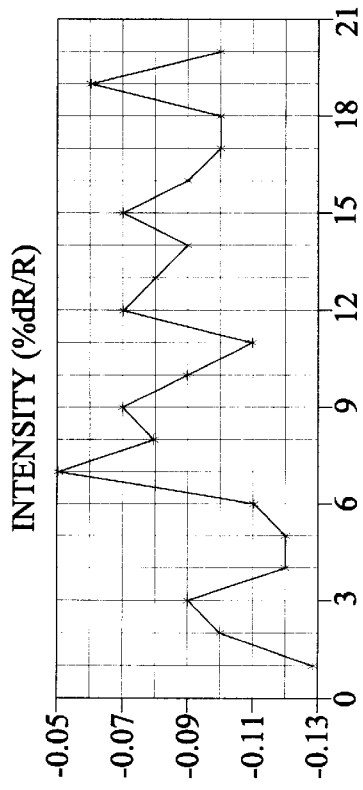
FIG. 7A
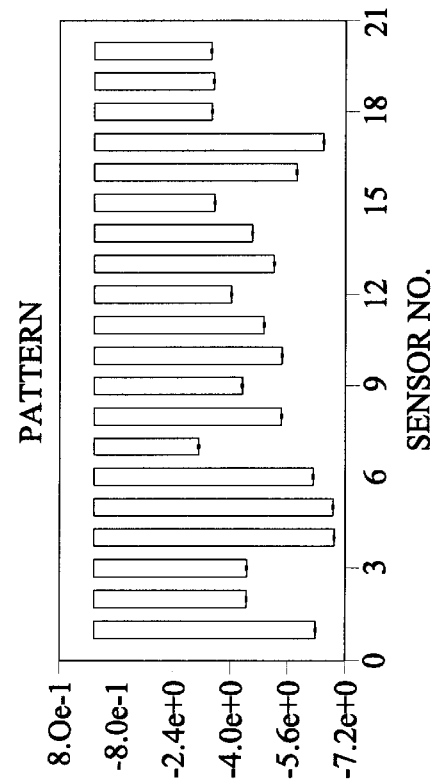
FIG. 7B

FIG. 9
REPORT
LAST FILE:
C:\QUESTAR\45MINS.DBA
1) 15 MINS
TILE005.RAW 48.97 to 90.38(s)
DATA PLOTTED
| SENSOR | INTENSITY | PATTERN | SD |
|---|---|---|---|
| 1 | 0.630 | 7.671 | 0.190 |
| 2 | 0.670 | 8.759 | 0.298 |
| 3 | 0.560 | 6.997 | 0.057 |
| 4 | 0.610 | 7.532 | 0.224 |
| 5 | 0.770 | 9.898 | 0.290 |
| 6 | 0.400 | 4.983 | 0.066 |
| 7 | 0.150 | 1.470 | 0.330 |
| 8 | 0.220 | 2.791 | 0.204 |
| 9 | 0.270 | 3.711 | 0.250 |
| 10 | 0.240 | 2.990 | 0.102 |
| 11 | 0.500 | 6.181 | 0.166 |
| 12 | 0.220 | 2.875 | 0.106 |
| 13 | 0.240 | 2.948 | 0.137 |
| 14 | 0.280 | 3.726 | 0.111 |
| 15 | 0.300 | 3.809 | 0.059 |
| 16 | 0.220 | 2.773 | 0.115 |
| 17 | 0.180 | 1.886 | 0.281 |
| 18 | 0.550 | 7.017 | 0.140 |
| 19 | 0.210 | 2.245 | 0.258 |
| 20 | 0.720 | 9.737 | 0.490 |
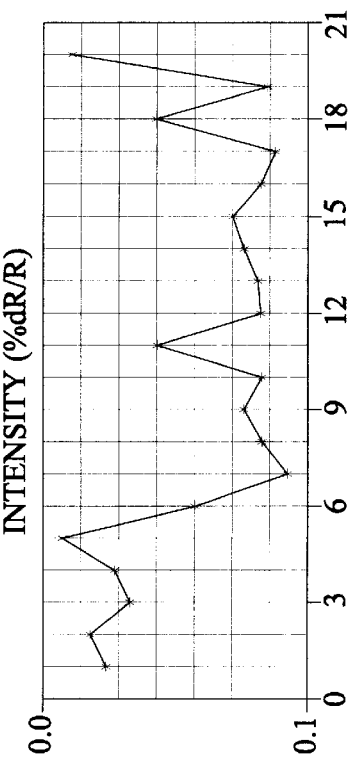
FIG. 9A
INTENSITY (%dR/R)
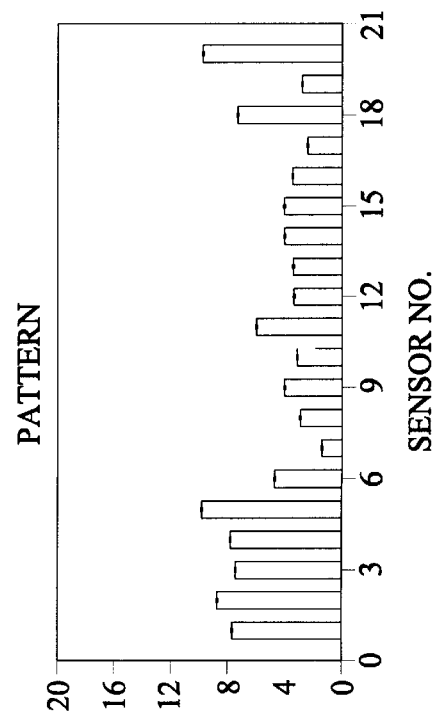
FIG. 9B
PATTERN
SENSOR NO.

FIG. 10
REPORT
LAST FILE:
C:\QUESTAR\45MINS.DBA
2) 45MINS
TILE006.RAW 56.18 to 108.38(s)
DATA PLOTTED
| SENSOR | INTENSITY | PATTERN | SD |
|---|---|---|---|
| 1 | 0.440 | 10.178 | 0.645 |
| 2 | 0.340 | 8.316 | 0.335 |
| 3 | 0.300 | 7.550 | 0.159 |
| 4 | 0.350 | 8.261 | 0.499 |
| 5 | 0.430 | 10.196 | 0.593 |
| 6 | 0.200 | 4.895 | 0.118 |
| 7 | 0.040 | 1.709 | 0.296 |
| 8 | 0.030 | 1.160 | 0.313 |
| 9 | 0.080 | 2.647 | 0.322 |
| 10 | 0.070 | 2.335 | 0.281 |
| 11 | 0.260 | 6.710 | 0.042 |
| 12 | 0.100 | 2.919 | 0.222 |
| 13 | 0.090 | 2.844 | 0.316 |
| 14 | 0.100 | 2.843 | 0.154 |
| 15 | 0.140 | 3.915 | 0.135 |
| 16 | 0.030 | 1.199 | 0.291 |
| 17 | 0.070 | 2.416 | 0.291 |
| 18 | 0.320 | 7.837 | 0.213 |
| 19 | 0.110 | 3.334 | 0.221 |
| 20 | 0.350 | 8.735 | 0.232 |
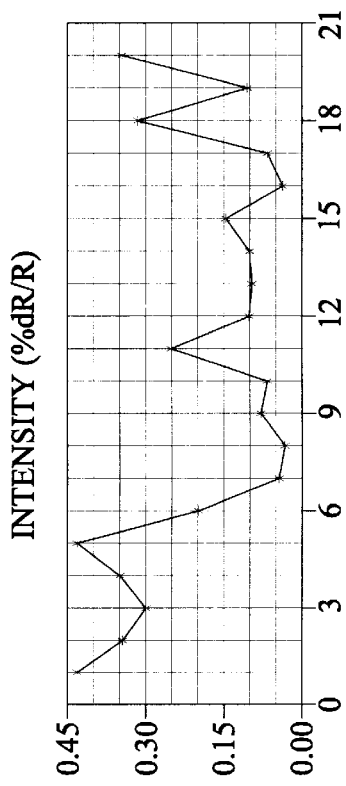
FIG. 10A
INTENSITY (%dR/R)
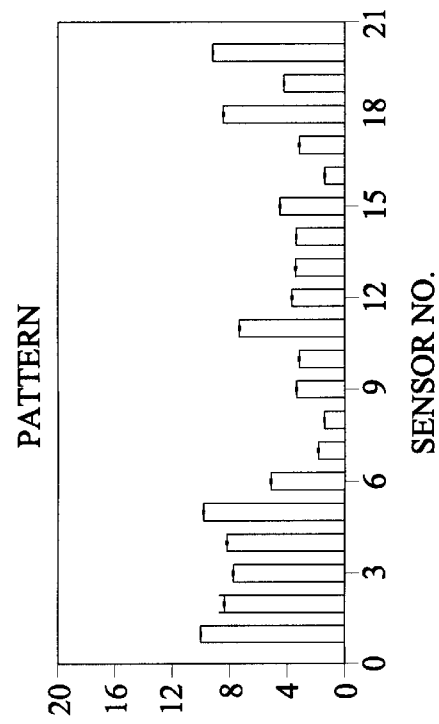
FIG. 10B
PATTERN
SENSOR NO.

FIG. 11
REPORT
LAST FILE:
C:\QUESTAR\45MINS.DBA
15MINS - 45 MINS
TILE005.RAW 46.97 to 90.38(s); TILE006
DATA PLOTTED
| Sensor | d_intensity | d_pattern | SD |
|---|---|---|---|
| 1 | 0.190 | -2.508 | 0.835** |
| 2 | 0.330 | 0.443 | 0.634 |
| 3 | 0.260 | -0.553 | 0.216** |
| 4 | 0.260 | -0.729 | 0.723 |
| 5 | 0.340 | -0.298 | 0.884 |
| 6 | 0.200 | 0.088 | 0.184 |
| 7 | 0.110 | -0.239 | 0.627 |
| 8 | 0.190 | 1.631 | 0.516** |
| 9 | 0.190 | 1.064 | 0.572 |
| 10 | 0.170 | 0.655 | 0.383 |
| 11 | 0.240 | -0.529 | 0.208** |
| 12 | 0.120 | -0.043 | 0.329 |
| 13 | 0.150 | 0.103 | 0.453 |
| 14 | 0.180 | 0.883 | 0.265** |
| 15 | 0.160 | -0.105 | 0.194 |
| 16 | 0.190 | 1.574 | 0.406** |
| 17 | 0.110 | -0.530 | 0.571 |
| 18 | 0.230 | -0.821 | 0.353** |
| 19 | 0.100 | -1.089 | 0.479** |
| 20 | 0.370 | 1.002 | 0.722 |
Euclidean distance: 4.289
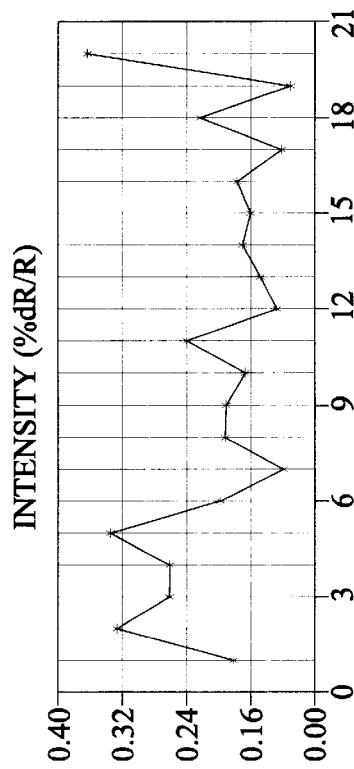
FIG. 11A
INTENSITY (%dR/R)
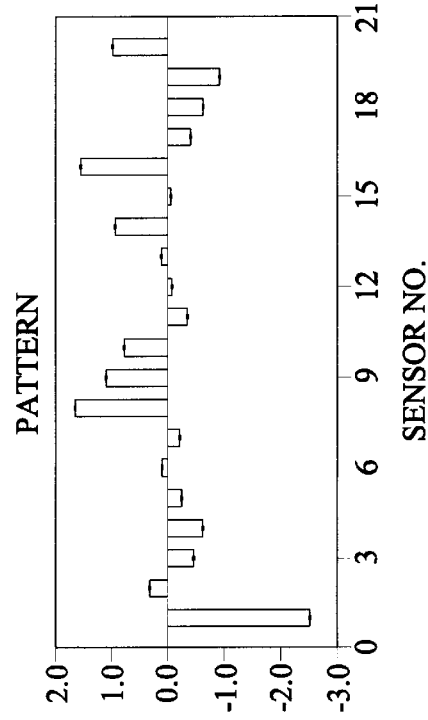
FIG. 11B
PATTERN
SENSOR NO.

METHOD FOR SUBSTRATE CLASSIFICATION

This application is the national phase of international application PCT/GB95/01118, filed May 18, 1995 which designated the U.S.

FIELD OF THE INVENTION

This invention relates to substrates and concerns a method of characterising substrates, particularly, but not exclusively, in relation to the behaviour of fragrances on substrates.

SUMMARY OF THE INVENTION

According to the invention there is provided a method of characterising a substrate by analysing properties of chemicals emanating from the substrate and/or from a substance applied to the substrate. The invention thus involves analysing the volatile chemical profile generated in the headspace over a substrate.

The properties of a substrate (including physical, chemical and microbiological properties) affect the behaviour of the substrate with respect to chemicals, particularly volatile chemicals, either naturally present in or on the substrate or in a substance applied thereto, and so affect the chemicals present in a headspace above the substrate. Accordingly, by analysing properties of chemicals emanating from the substrate (or a substance applied thereto) information can be obtained on the nature of the substrate which can be used to characterise the substrate.

The invention can be applied to a wide range of substrates, including, for example, skin, wood, hair, clothing, carpets, plastics surfaces, ceramic tiles, wool, fabric, perfumed products such as soap, detergents etc.

For example, human skin is conventionally characterised by reference to a number of descriptors including the following:

Greasy

Moisture content (high/low)

Ethnic group

Tanning ability

Sensitivity to break out

Bacterial count (high/low)

Age of skin

Hair level

Surface morphology (roughness)

Lesions/abrasions

Healthy/unhealthy (eg dermatitis)

Such factors affect the behaviour of skin with respect to chemicals, so that skin can be characterised with reference to one or more of these factors, with complex, composite characterisations by reference to several factors being possible.

Having characterised a particular substrate by the method of the invention, eg. oily skin, ceramic tile, a particular detergent product etc, products (generally a fragrance or fragrance-containing product) having desired optimised properties particularly suited for use with that substrate can be determined. In this way products with optimum components and physical and chemical characteristics to perform within defined environments and conditions on a particular substrate can be developed. Selection of suitable products can be made by trial and error, with a degree of prediction being possible based on a knowledge of the performance of the substrate under consideration and also using convention formulation techniques. For example, it is known that certain cosmetic products are better suited to use on particular skin types. For fragrances or fragrance-containing products (eg skin, hair, fabric cleaning, hard surface cleaning products etc), it will generally be desirable to provide a long lasting perfume. For shampoos, high perfume impact during use is generally the desired objective. For malodour counteractancy products, effective malodour masking is the desired aim.

Examples of products that can be formulated in this way include, but are not limited to, fine fragrances, after-shaves, cosmetics, deodorants, soaps, shampoos, air-fresheners, furniture polishes, hard-surface cleaners, fabric-conditioners, laundry detergents, smooth washes, toothpastes, shower gels etc.

Having characterised a range of substrates, eg skin types, by use of the invention, an unknown substrate, eg skin of unknown type, can be classified by comparison with data for known types. This may then provide guidelines for the most appropriate treatment for that substrate.

The method of the invention may be applied to a substrate on its own, with analysis being made of chemicals naturally emanating from the substrate, or to a substrate to which a test formulation has been applied, with analysis being made of properties of chemicals emanating from both the substrate and the test formulation which are thus influenced by the interaction between the substrate and test formulation. For testing skin, for example, it would be suitable to use a test formulation comprising a mixture of volatile chemicals selected for maximum variation of behaviour over a range of skin types. A typical test formulation would comprise a mixture of equal weights of the following:

Benzyl acetate

Dimethyl benzyl carbonol acetate

Hydroxycitronellal

Iso amyl salicylate

Linalol

Methyl ionone, alpha iso

Phenyl acetaldehyde dimethyl acetal beta Pinene

Styrallyl acetate as a 2 to 5% solution in an eau de cologne base.

The analysis is preferably made using a volatile chemicals sensor. A range of suitable sensors is known and commercially available. Known sensors typically comprise an array or arrays of sensors which produce signals modulated by the adsorbance of volatile chemicals. Sensors suitable for use in such arrays include the following:

metal oxide gas sensors catalytic gas sensors organic semiconducting gas sensors, particularly conducting polymers solid electrolyte gas sensors mass sensitive devices, such as piezoelectric quartz crystals fibre-optic probes electrochemical sensors MOSFET sensors Langmuir-Blodgett film sensors.

Volatile chemicals sensors are discussed in her detail in "Multielement Arrays for Sensing Volatile Chemicals" by K C Persaud and P Travers in Intelligent Instruments and Computers, July–August 1991, Vol. 9(4) pp 147–154, and "Electronic gas and odour detectors that mimic chemoreception in animals" by K C Persaud in Trends in Analytical Chemistry, 1992, Vol. 11(2) pp 61–67.

It is currently preferred to use a sensor comprising an array of conducting polymers, eg an AromaScanner device available from AromaScan pic or similar equipment available from Neotronics Ltd. The AromaScanner device, for example, contains an array of semi-conducting polymers (typically having 20 or 32 elements in the array), the electrical resistance of which is claimed to alter rapidly and reversibly by the surface adsorption of volatile chemicals. The change in resistance in the elements is measured continuously and the results processed by an associated computer system using software provided to produce a map (or "fingerprint") of volatile chemicals, eg as a graph, bar chart or in other convenient form. The computer system may be any digital datalogging and processing apparatus with appropriate peripherals capable of multivariate analysis, screen and/or hard copy presentation, and conveniently comprises a personal computer such as an IBM PC or similar with suitable peripherals.

The data represented by the maps or odour images produced in this way may be analysed by techniques of multivariate statistics, eg using known techniques such as Euclidian distance mapping and principal component analysis, to present the data in a form that is more easily handled for comparison purposes. In addition, sensor responses may usefully be analysed by learning techniques, eg based on neural networks and fuzzy logic, leading not only to odorant detection but also recognition.

The invention has a number of possible specific applications, including the following:

1) Characterisation of an unknown substrate by reference to previously obtained results for known substrates. One example of this is characterisation of skin types. It is envisaged this could be offered as a service for consumers, eg in the cosmetics departments of shops. Having classified a customer's skin type, the customer can then be offered cosmetic products particularly designed for that skin type.

2) Having characterised a substrate, eg skin type, products for use on that substrate can be tested on that substrate using gas analysis sensors and formulated for optimised performance on that substrate, eg to provide a long lasting perfume of the desired odour character.

3) Malodour counteractancy. A gas sensing system may be taught to recognise a malodour and detect when it is likely to be perceived at significantly unpleasant levels. The efficacy of a perfume at masking/counteracting an unpleasant odour can then be measured, eg a measure of deodorant perfume or flavour activity. This could supplement and/or replace use of in vivo sensory panels, as described eg in Whitehouse and Carter as published in The Proceedings of the Scientific Section of the Toilet Goods Association, No 18, pp 31–37. In particular, this approach can be used to optimise the formulation of fragrances/deodorants where such formulations are intended to reduce malodour caused by microbial breakdown of eg steroids and lipids. As in 2), perfume performance in respect of desired hedonics (eg pleasant floral note) may also be optimised. However, in the case of the human axillae, the "substrate" is changing (eg heat, amount of perspiration, bacterial count, etc) and it is important to gather data at appropriate points in the product life-cycle, eg 12-hour performance of deodorants.

4) Perfume delivery. Efficiency of perfume delivery, such as from a hard surface cleaner where perfume is present in the air at very low levels, may be monitored. The gas sensors appear to be capable of detecting very low levels of volatile chemicals and might prove invaluable in instances where conventional headspace gas chromatography is at the detection limits.

The approach could also be used to monitor the efficiency of perfume delivery systems such as those in which perfume is carried in a starch matrix for subsequent release. This approach is used, eg, in deodorants, with the perfume staying in the starch matrix until the user starts sweating. Upon contact with moisture, the perfume is released from the starch matrix. The gas sensor could be used to monitor on a continuous basis the release of perfume in this context.

5) Substantivity on skin, hair and cloth. Olfactory assessments using a panel of experts can be highly subjective, particularly in this area where odours assessed are often at threshold levels. A gas sensor could provide an objective evaluation of substantivity, working in parallel with panels of perfumers. Once a definite profile is established, a rapid evaluation of substantivity on, eg skin, hair, cloth, can be carried out without a team of evaluators.

6) Odour evaluation from skin. A method of skin characterisation via perfume can be developed, following skin characterisation by the method of the invention.

BRIEF DESCRIPTION OF THE DRAWINGS

The invention will be further described, by way of illustration, in the following Examples which refer to the accompanying drawings, in which:

FIGS. 2 to 7 are a series of odour profile reports obtained from a conducting polymer sensor array of results from various test pieces of terry towelling;

FIGS. 9 and 10 are odour profile reports of the same form as those of FIGS. 2 to 7 with results from ceramic tiles cleaned with perfumed hard surface cleaner after 15 and 45 minutes airing, respectively;

FIG. 11 is a comparison of the results of FIGS. 9 and 10, showing the difference in "odour image"

EXAMPLE 1

Experiments were preformed on pieces of terry towelling, approximately 250 mm square.

A piece of untreated terry towelling and pieces washed in laundry product with or without various perfumes were all analysed using an instrument from AromaScan plc. The sensing device in this instance had an array of 20 conducting polymer sensors, and was used in conventional manner, in accordance with instructions from the supplier.

Each test piece of terry towelling (after washing and drying if appropriate) was placed in a respective plastic bag. The bag was sealed, filled with filtered air and allowed to equilibrate for at least 30 minutes: Air was then extracted from the bag and supplied to the sensor.

Figure 1:
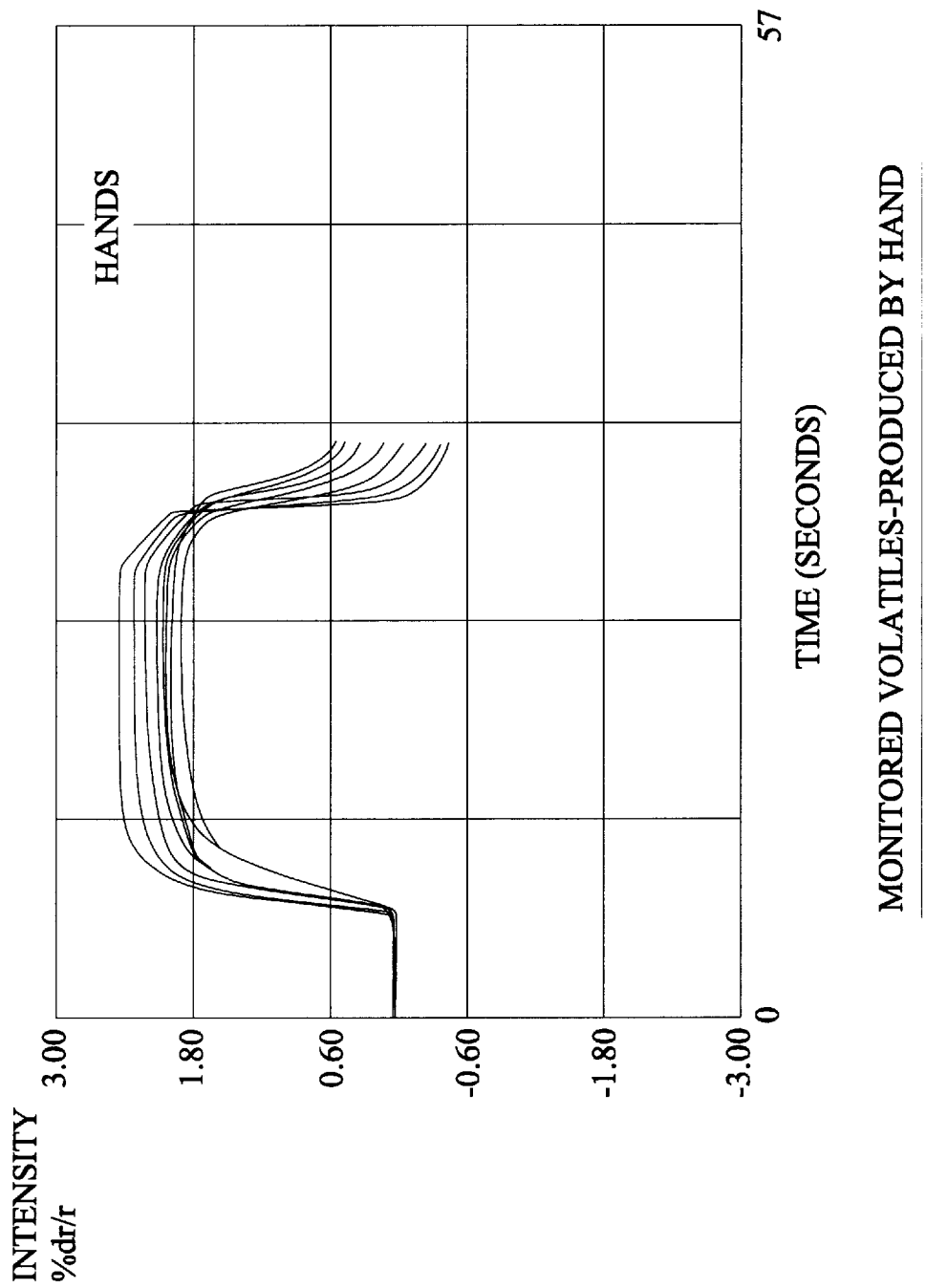
FIG. 1 is a graph of resistance (% dR/R) versus time (in seconds) produced by hand volatiles using a conducting polymer sensor array.

The resistance output from each sensor varies with time, and a typical plot of such raw data (from a hand, rather than one of the test pieces of terry towelling) is shown in FIG. 1, with each line plotted representing the variation in resistance of one of the 20 sensors in the array with time. It will be seen that the sensor provides continuous monitoring of the sensor output with time.

To provide data in a more manageable form, a computer associated with the sensor is programmed to provide data in the form of a report giving information relating to a particular time span, selected by the operator or the computer to give representative results. Such reports can be obtained at spaced intervals in time as desired, eg approximately every 15 minutes, to provide information on changes in odour profile with time.

An odour profile report of this sort with results for an untreated test piece of terry towelling is included as FIG. 2, with the resistance data for each sensor given numerically and graphically.

In FIG. 2 data is given for the time span after the start of the test indicated in the heading (53.78 to 109.27 seconds), with data for odour intensity, pattern and standard deviation (SD) given in the table. The "odour pattern" is formed by the normalised sensor responses to the odour. The "intensity" is the percentage resistance change over the base resistance for each sensor (% dR/R). The intensity and pattern data are also shown graphically in FIGS. 2a and 2b, respectively.

FIGS. 3 to 7 are odour profile reports of the same form as FIG. 2 and give data for respective pieces of terry towelling washed in laundry products with various different perfumes AA, CC, DD and EE, and in an unperfumed laundry product (FF) for the time spans specified on the reports.

Figure 8:
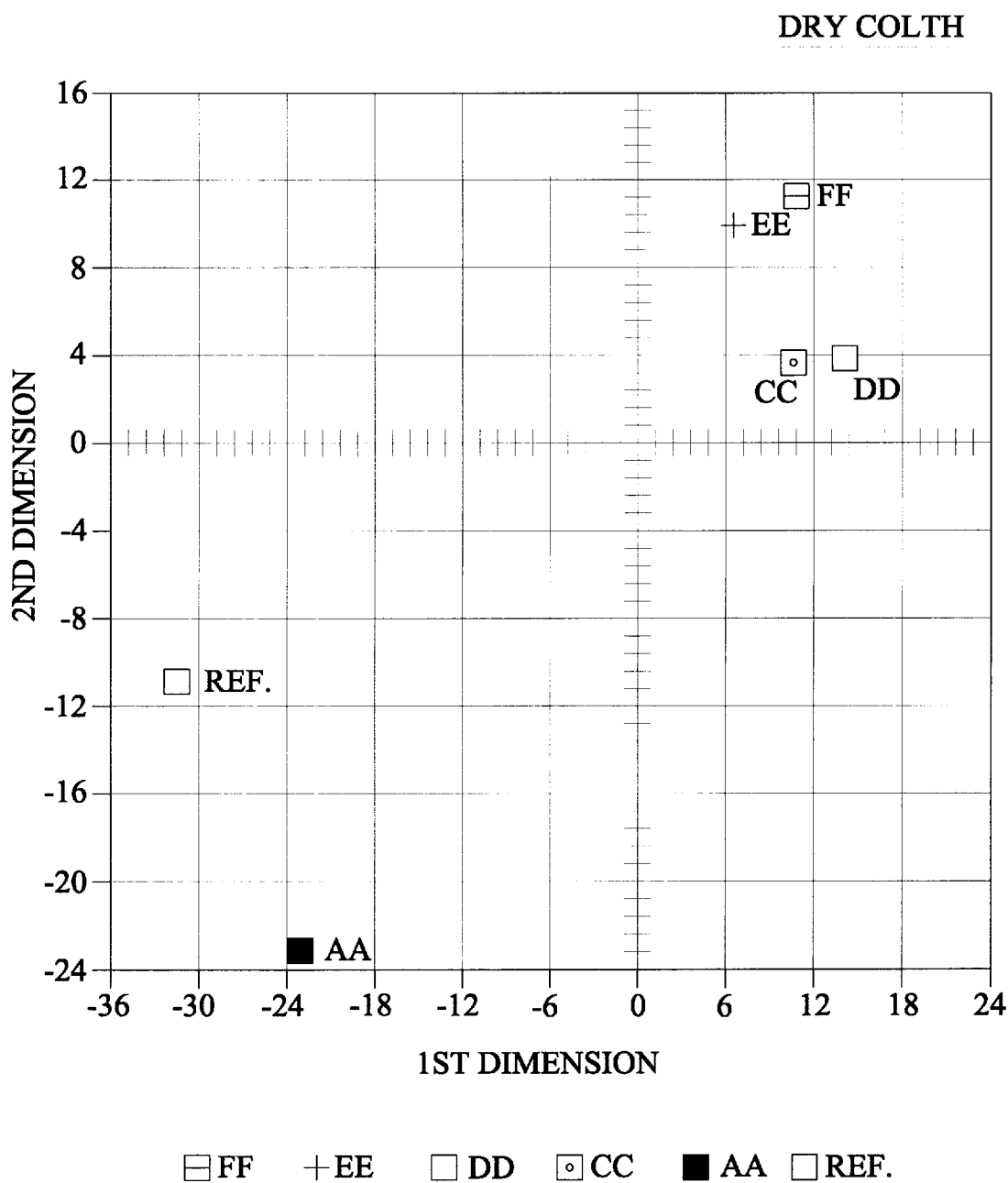
FIG. 8 is a graph summarising the data in FIGS. 2 to 7, obtained by Euclidian distance mapping.

For ease of handling and comparison, this data was statistically analysed by the technique of Euclidian distance mapping to produce a single 2-dimensional graph with a series of points, each representing results for one of the samples. The resulting graph is included as FIG. 8. It will be seen the points for samples washed in laundry products with perfumes CC, DD and EE and unperfumed product FF form a cluster of distinct points, while those using perfume AA and those for the unwashed sample (marked ref) are spaced well away. Each sample thus produces a characteristic, distinctive result which can be used to characterise the sample.

EXAMPLE 2

A further series of experiments, similar to those described in Example 1, was performed on a pair of similar 7.5×7.5 cm ceramic tiles, identically treated with a perfumed hard surface cleaner (Fabulaso, Lavandar). After treatment, the two tiles were exposed to ambient atmosphere for 15 and 45 minutes, respectively. The two tiles were then placed in respective glass jars which were filled with filtered air, sealed and allowed to equilibrate for 1 hour. Headspace air was then extracted from the first jar and supplied to the AromaScan instrument for analysis. The resulting odour profile report (after 15 minutes exposure) is shown as FIG. 9. The maximum intensity (% dR/R) measured was nearly 0.8.

A further odour profile report (after 45 minutes exposure) was similarly obtained from the second jar, and this is shown in FIG. 10. Here the maximum intensity measured is about 0.45, nearly half that measured after 15 minutes.

FIG. 11 is a comparison of the results after 15 and 45 minutes. This shows that there is not only a change in intensity, but also a change in odour pattern over time.

EXAMPLE 3

Similar experiments can be performed with biological substrates such as skin and hair. In experiments to characterise skin, water-cleansed skin of a specific area of the inner forearm of a number of subjects drawn from within one ethnic group was assessed with and without applied perfume, on this occasion using a dynamic method (no equilibration), often referred to as "odour stripping".

A collecting vessel was strapped to the inner forearm of the subject to form an air-tight enclosure. The collecting vessel may be of any material which is inert and impermeable to volatiles. Suitable materials include glass, PTFE and polyamide. It is important to ensure a good seal with the skin when sampling. A poor seal is readily detected by an unstable signal. If necessary, a gasket may be used to improve the seal. Filtered, humidity controlled air was passed over the designated skin area and into an AromaScan 32-sensor machine (from AromaScan plc). The machine is generally similar to that used in the previous examples (but has 32 sensors instead of 20) and has an associated computer system. A strict protocol was observed comprising three cycles, with two sampling cycles and a wash cycle. A "cycle" refers to the reference air—sample air—reference air valve sequence. The sensor-response data generated during the second sampling cycle was stored for analysis. It is important to use the same time slice from each subject. The size of the time-slice was selected by consideration of the stability of the readings at the end of the cycle(s) and determined empirically. In these experiments the time-slice was 30 seconds, but this is not critical.

Tests were made on each subject, with and without applied perfume (in the form of a 2% cologne, 50 μl per test area). The perfume formulation used in the cologne is as follows:

|  | Percent |
|---|---|
| Benzyl acetate | 40.00 |
| Hydroxycitronellal | 5.00 |
| Ionone alpha | 10.00 |
| Linalol | 25.00 |
| Linalyl acetate | 16.00 |
| Rhodinol | 4.00 |
|  | 100.00 | as a 2% solution in an eau de cologne base.

In cases where cologne was applied, sensing was effected by the sensing machine 30 minutes after application of the cologne.

In tandem with the machine sensing, an exercise was carried out concurrently (or repeated) utilising the skills of an experienced perfumery team. The other arm of the subject was prepared in an identical manner to the first arm of at the end of the instrumental assessment (or after 25 minutes, according to the chosen method). Both arms were then assessed and compared 5 minutes and 30 minutes respectively after the two cologne applications.

Figure 12:
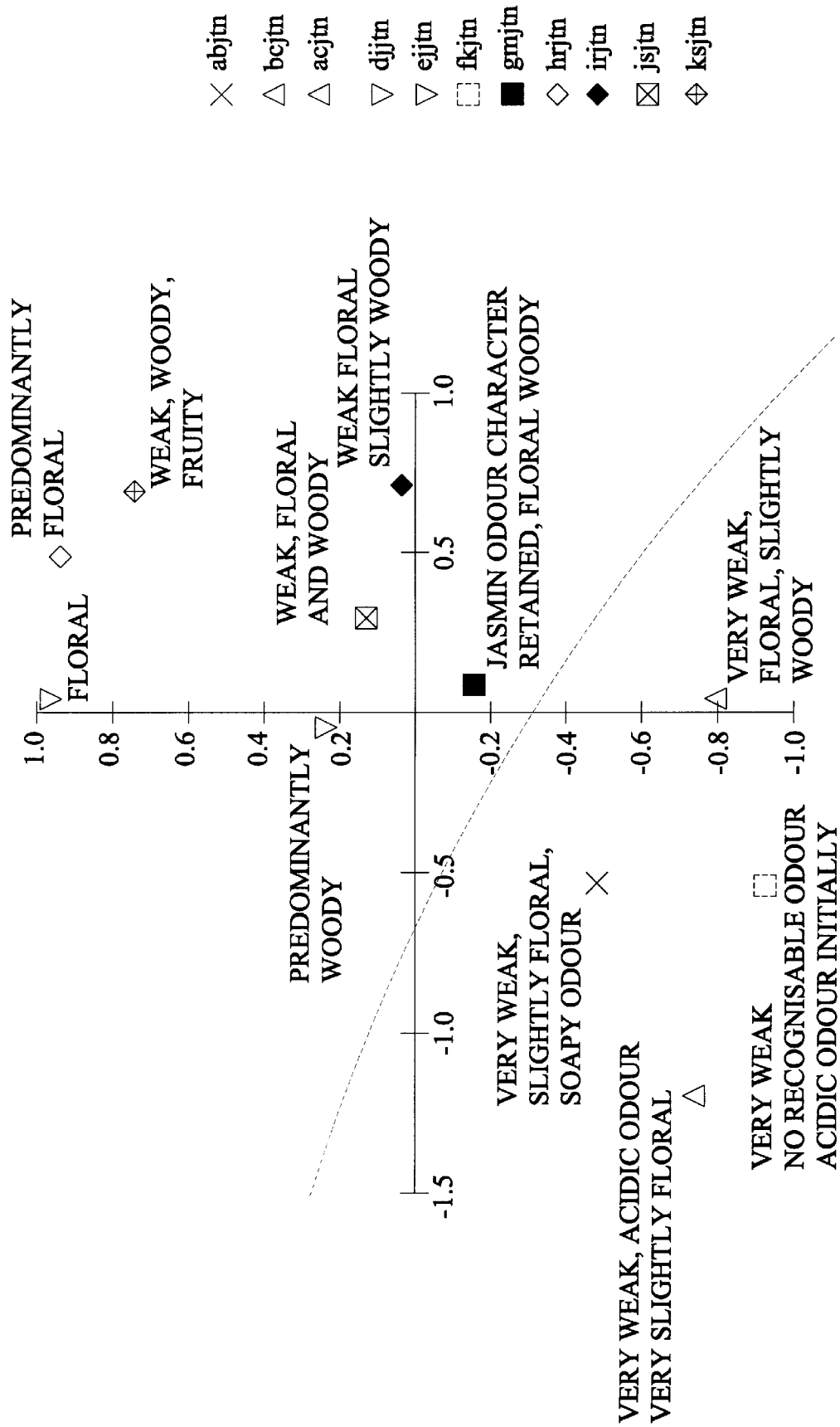
FIG. 12 is a 2-dimensional representation of sensor data obtained from a group of subjects treated with a cologne perfume.

The data from this experiment may be analysed using a variety of methods, for examples non-linear mapping, principal component analysis, and neural networks. FIG. 12 depicts a two dimensional map, generally similar to FIG. 8, derived using non-linear mapping based on the algorithm developed by J W Sammon, described in IEEE Transactions on Computers, Vol. C. 18(5) pp 401–4091. Each symbol on the map represent results for one of the subjects. FIG. 12 also summarises the sensory evaluation results on the group of subjects, giving odour descriptions for the subjects. It is clear that two major sets can be discerned, comprising those whose skin retains little of the perfume after 30 minutes (bottom left of the dotted line), and those whose skin retained a clearly perceptible perfume note. Within this seconds set, the characteristic notes discerned were woody, floral, fruity and jasmin, and there are indications that these will also form discrete subsets.

A subject with unknown skin type can then be tested in a similar way, and by comparing the results with those for the known standard skin types, the unknown skin type an be classified and characterised. This step may be performed as a service to consumers, eg being performed by suitably trained but non-expert personnel in a beauty salon, cosmetics shop or department etc, using equipment specially supplied for this purpose. Results can be obtained relatively quickly, possibly after 15 minutes or less, so a customer could be provided with a "while you wait" skin classification service.

With a knowledge of the customer's skin type, the customer can then (immediately or at a later occasion) be offered cosmetic or fragrance products designed to be particularly suited to that skin type.

We claim:

1. A method of characterising a substrate which comprises
    applying a test formulation to said substrate, subsequently collecting volatile chemicals in a headspace above the substrate,
    determining a profile of the volatile chemicals so emanated, and
    using said profile to characterise the substrate.

2. A method according to claim 1, wherein the substrate comprises skin, wood, hair, clothing, carpets, plastics surfaces, ceramic tiles, wool, fabric or, perfumed products.

3. A method of formulating a product of use on a particular substrate which comprises characterizing said substrate by the method of claim 1, selecting components having physical and chemical characteristics to perform on said substrate, the selection of said components being based on a knowledge of the performance of the substrate as determined by the method of claim 1 and formulating said product from said components.

4. A method according to claim 3, wherein the product comprises a fine fragrance, after-shave, cosmetic product, deodorant, soap, shampoo, air-freshener, furniture polish, hard-surface cleaner, fabric-conditioner, laundry detergent, mouth wash, toothpaste or, shower gel.

5. A method according to claim 3, wherein the component is a fragrance or a cosmetic ingredient.

6. A method according to claim 1, wherein human body odour is determined following treatment of the body with a deodorant product.

7. A method according to claim 1, wherein a substrate of unknown type is classified by comparing characterising information obtained by the method of the invention with previously obtained characterising information for a range of known substrates.

8. A method according to claim 1, wherein a test formulation is applied to the substrate prior to analysis.

9. A method according to claim 8, wherein the test formulation comprises a mixture of volatile chemicals.

10. A method according to claim 1, wherein the chemicals are analysed using a volatile chemicals sensor.

11. A method according to claim 10, wherein the sensor comprises an array of conducting polymer sensors.

12. A method according to claim 1, wherein chemical analysis data is statistically analysed.

* * * * *